United States Patent
Koike et al.

(10) Patent No.: US 10,926,045 B2
(45) Date of Patent: Feb. 23, 2021

(54) MESH NEBULIZER AND REPLACEMENT MEMBER

(71) Applicant: OMRON HEALTHCARE CO., LTD., Muko (JP)

(72) Inventors: Tadashi Koike, Kyoto (JP); Nobuhiko Osoegawa, Kyoto (JP); Yukiko Mitsunami, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 286 days.

(21) Appl. No.: 16/168,881

(22) Filed: Oct. 24, 2018

(65) Prior Publication Data

US 2019/0054258 A1   Feb. 21, 2019

Related U.S. Application Data

(63) Continuation of application No. PCT/JP2017/016772, filed on Apr. 27, 2017.

(30) Foreign Application Priority Data

May 9, 2016 (JP) .............................. JP2016-094028

(51) Int. Cl.
*A61M 11/00* (2006.01)
*B05B 17/06* (2006.01)
(Continued)

(52) U.S. Cl.
CPC ........... *A61M 11/005* (2013.01); *A61M 11/00* (2013.01); *A61M 15/0085* (2013.01);
(Continued)

(58) Field of Classification Search
CPC .... A61M 11/00; A61M 11/005; A61M 15/00; A61M 15/0085; B05B 17/06;
(Continued)

(56) References Cited

U.S. PATENT DOCUMENTS

2004/0050953 A1* 3/2004 Terada ................ B05B 17/0623
239/102.2
2014/0231538 A1* 8/2014 Tabata ................ B05B 17/0638
239/102.1
(Continued)

FOREIGN PATENT DOCUMENTS

CN          103826758 A      5/2014
JP          2014-004208 A    1/2014
WO          02/28545 A1      4/2002

OTHER PUBLICATIONS

Official Communication issued in corresponding Chinese Patent Application No. 201780029023.7, dated Jun. 28, 2020.
(Continued)

*Primary Examiner* — Joseph D. Boecker
(74) *Attorney, Agent, or Firm* — Keating and Bennett, LLP

(57) ABSTRACT

A mesh nebulizer includes a main body including a recess with a shape that is open upward. The main body includes a vibration portion with a vibration surface, and a liquid supply portion that supplies the liquid onto the vibration surface. The mesh nebulizer also includes a cap that openably and closeably covers the upper portion of the main body, and a replacement member that is separate from the main body and the cap and detachably mounted in the recess of the main body in advance when the nebulizer is to be used. The replacement member includes a film mesh portion, a bottom plate portion, and a side wall portion. When the cap is closed with respect to the main body, the protrusion portion of the cap presses the bottom plate portion of the replacement member toward the bottom surface of the recess, thus positioning the replacement member in the vertical axis direction of the main body.

12 Claims, 15 Drawing Sheets

(51) Int. Cl.
  *A61M 15/00*   (2006.01)
  *B05B 17/00*   (2006.01)
(52) U.S. Cl.
  CPC ............ *B05B 17/06* (2013.01); *B05B 17/063* (2013.01); *B05B 17/0638* (2013.01); *A61M 15/0021* (2014.02); *A61M 2205/8206* (2013.01)
(58) Field of Classification Search
  CPC ............ B05B 17/0607; B05B 17/0623; B05B 17/063; B05B 17/0638; B05B 17/0646
  See application file for complete search history.

(56) References Cited

U.S. PATENT DOCUMENTS

2016/0193434 A1\* 7/2016 Gleixner ............... A61M 39/24
                                             128/200.16
2016/0271343 A1\* 9/2016 Abate .................. A61M 11/001
2019/0192791 A1\* 6/2019 Osoegawa ............. A61M 11/00

OTHER PUBLICATIONS

Official Communication issued in International Patent Application No. PCT/JP2017/016772, dated Aug. 1, 2017.

\* cited by examiner

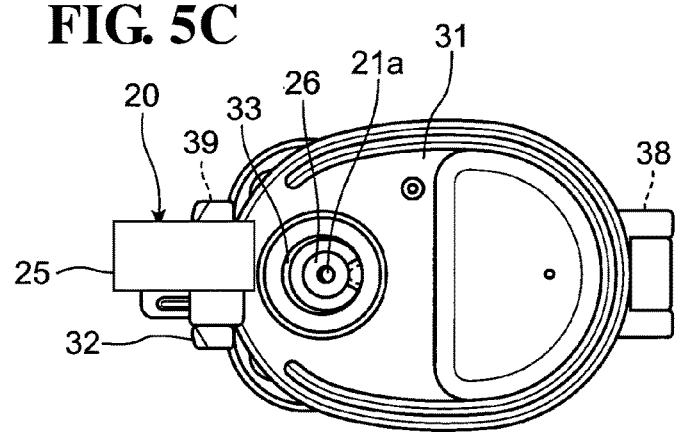
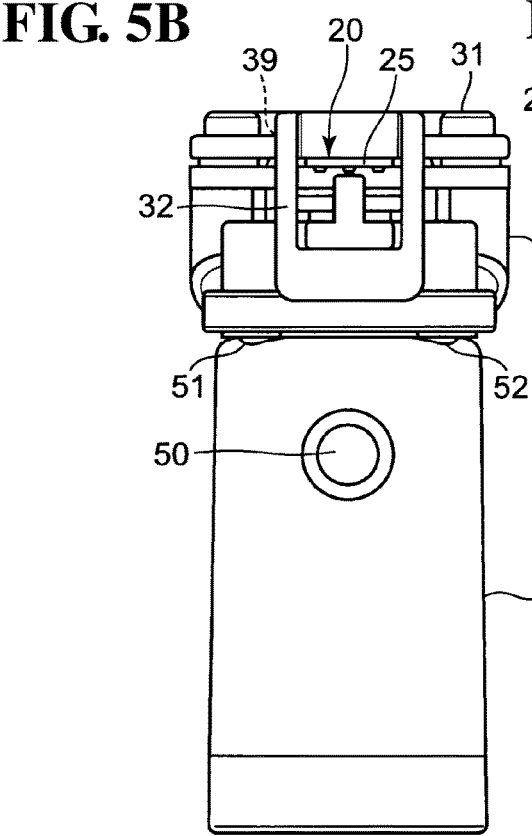
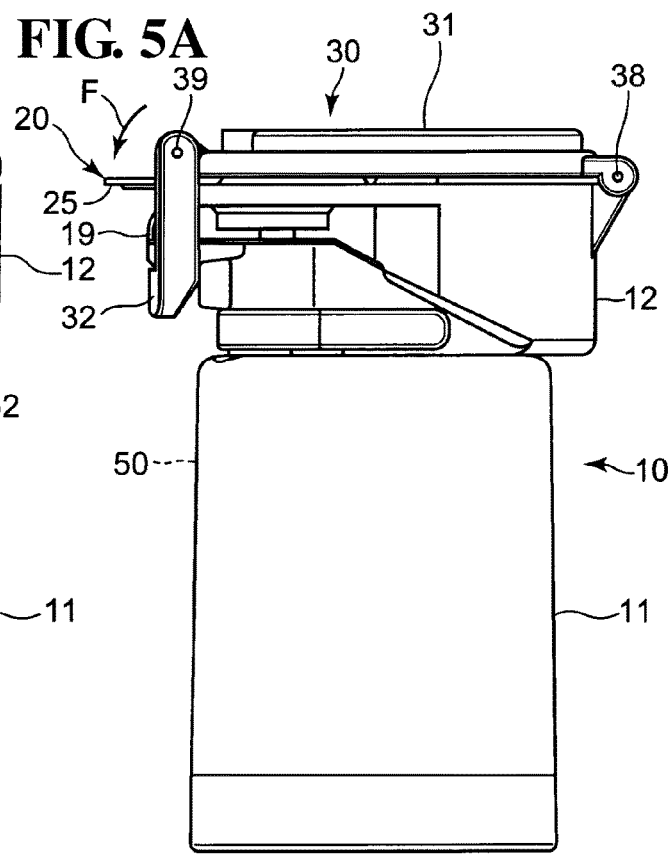

FIG. 8B    FIG. 8A    FIG. 8C
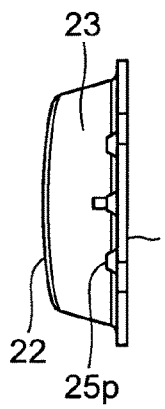
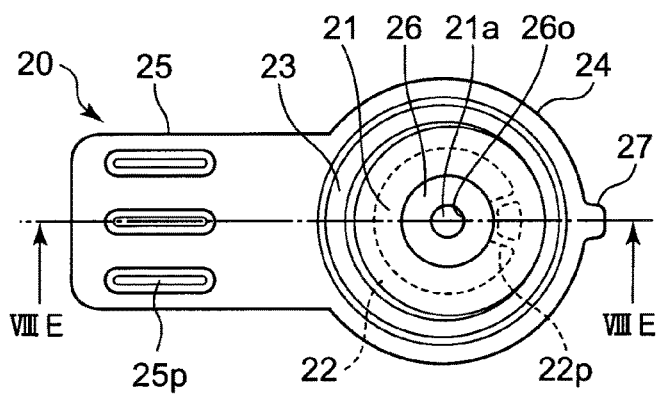
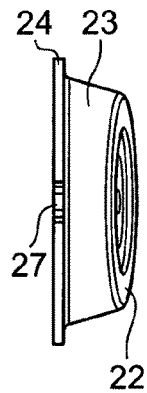
FIG. 8D
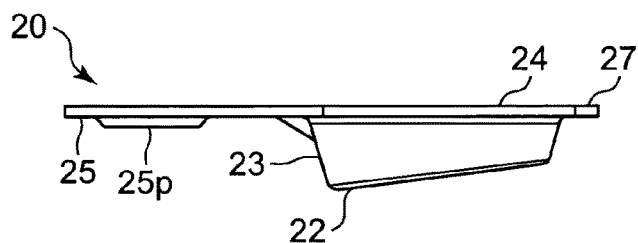
FIG. 8E
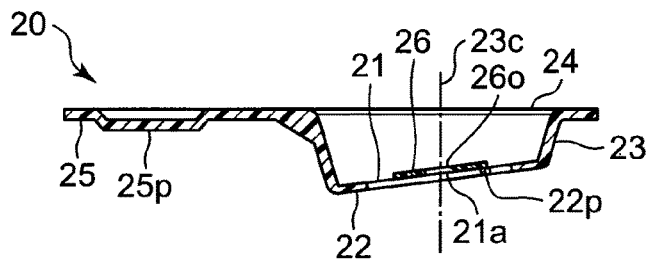
FIG. 8F
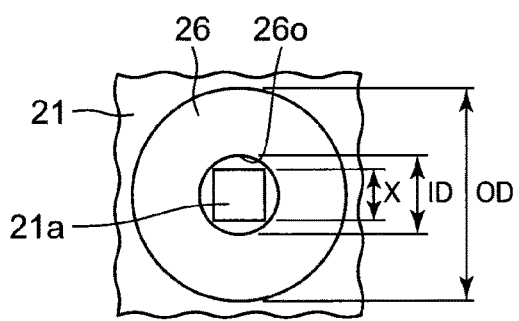

FIG. 12B FIG. 12A FIG. 12C
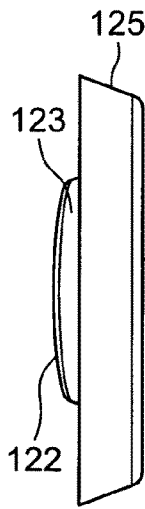
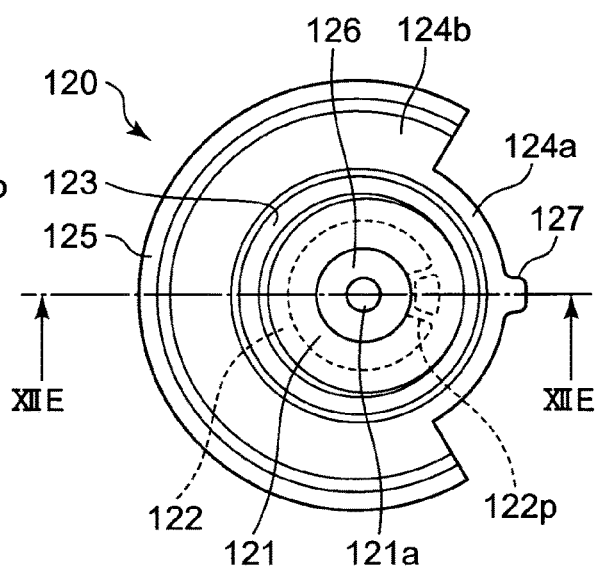
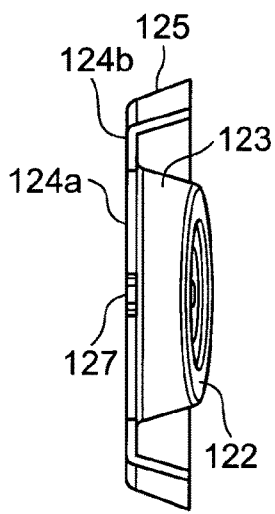
FIG. 12D
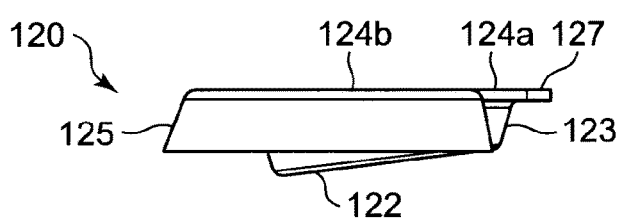
FIG. 12E
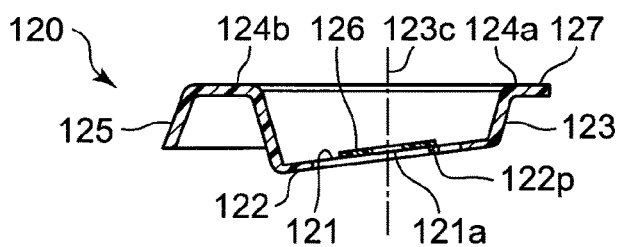

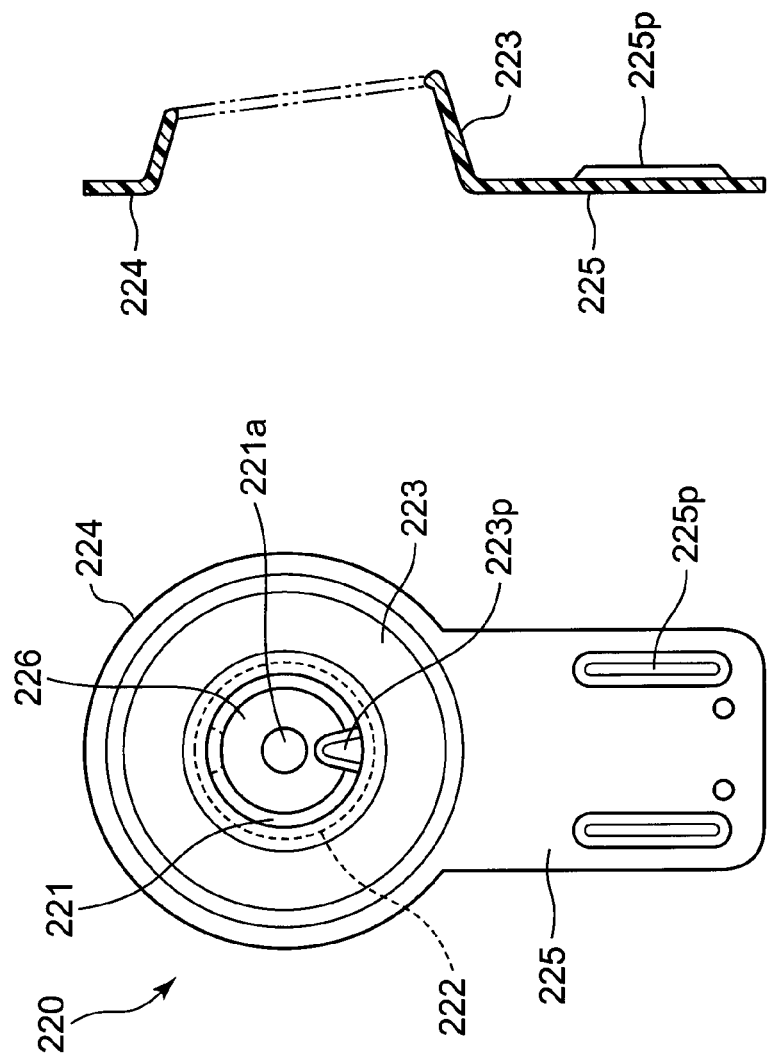

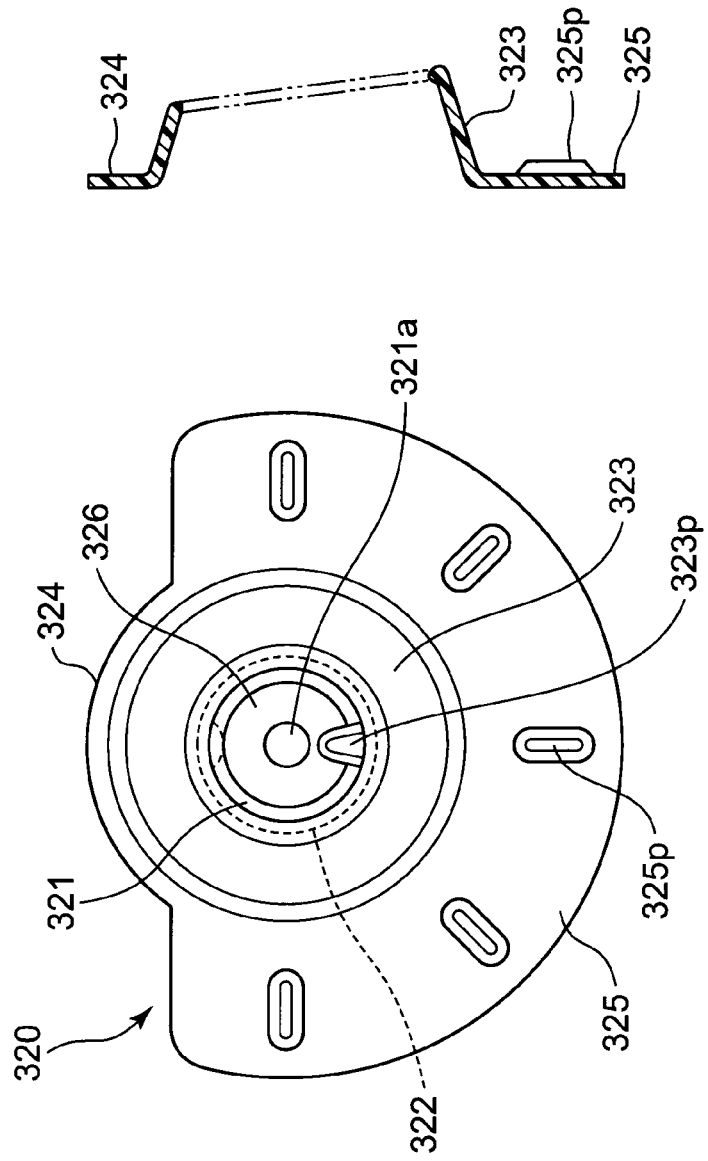

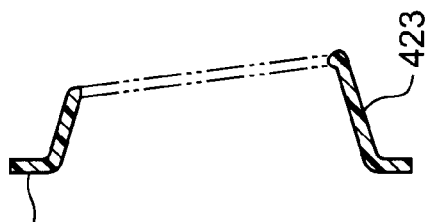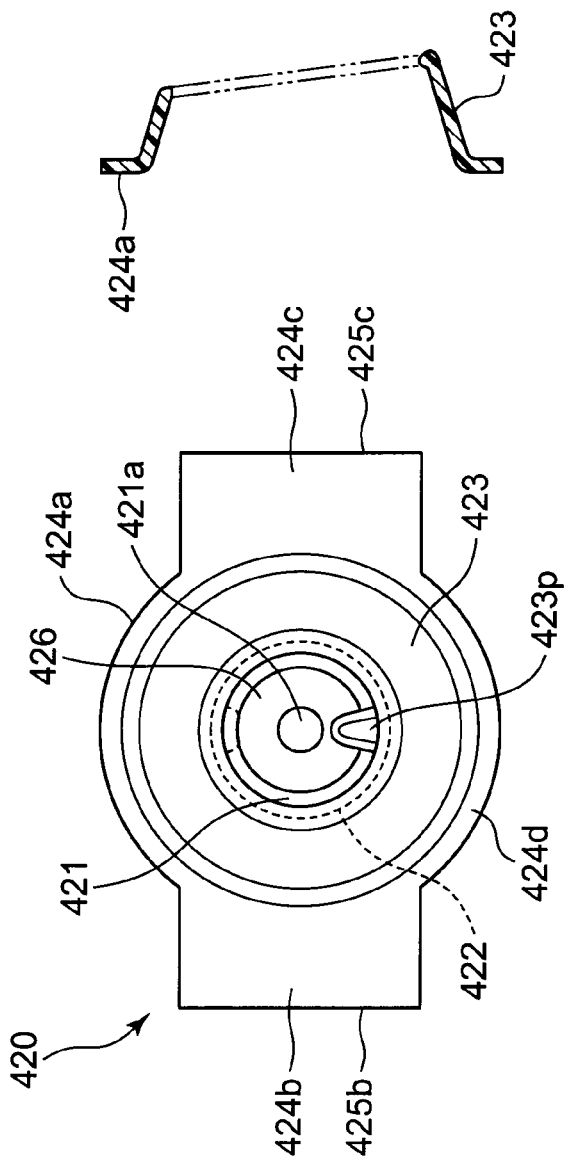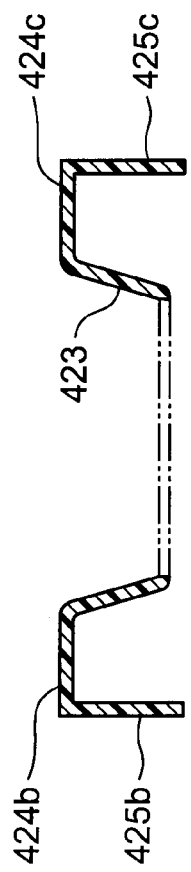

MESH NEBULIZER AND REPLACEMENT MEMBER

CROSS REFERENCE TO RELATED APPLICATIONS

This application claims the benefit of priority to Japanese Patent Application No. 2016-094028 filed on May 9, 2016 and is a Continuation Application of PCT Application No. PCT/JP2017/016772 filed on Apr. 27, 2017. The entire contents of each application are hereby incorporated herein by reference.

BACKGROUND OF THE INVENTION

1. Field of the Invention

The present invention relates to a mesh nebulizer, and more specifically relates to a mesh nebulizer that nebulizes and ejects a liquid supplied between a vibration surface and a mesh portion, through the mesh portion.

Also, the present invention relates to a replacement member that is used to form this kind of mesh nebulizer.

2. Description of the Related Art

Conventionally, as this kind of mesh nebulizer, as disclosed in JP 2014-4208A, a mesh nebulizer has been known which includes a horn vibrator in a main body and a mesh cap that is attached to the main body so as to be detachable and so as to be able to open and close (rotate). In the state in which the mesh cap is attached to the main body and is closed, the vibration surface of the horn vibrator and the mesh portion of the mesh cap oppose each other. In this state, medicinal liquid is supplied between the vibration surface and the mesh portion, and a driving voltage is applied to the horn vibrator, whereby the vibration surface is vibrated. Accordingly, the medicinal liquid is nebulized and ejected through the mesh portion.

However, with the above-described mesh nebulizer, every time after use, the mesh cap needs to be removed from the main body and the mesh cap including the mesh portion needs to be cleaned, disinfected, and dried. For this reason, there is a problem in that maintenance is troublesome for the user. Also, since the mesh portion including the mesh portion is a consumable article, it normally needs to be replaced in about one year, even if the user has been maintaining it correctly. Since the mesh cap is relatively large and expensive, there is a problem in that the cost burden for the replacement member is large for the user. Note that if the mesh cap has not been cleaned correctly, the nebulization efficiency will decrease, and the mesh cap will be unhygienic. Also, since the mesh cap is a precision article, cleaning is difficult.

SUMMARY OF THE INVENTION

In view of this, preferred embodiments of the present provide mesh nebulizers that are easy for a user to maintain, and for which the cost burden for a replacement member is small.

Also, preferred embodiments of the present invention provide replacement members included in such mesh nebulizers.

A mesh nebulizer according to a preferred embodiment of the present invention includes a main body including a recess with a shape that is open upward, the main body including a vibration portion with a vibration surface arranged at a position corresponding to a bottom surface of the recess, and a liquid supply that supplies liquid onto the vibration surface of the vibration portion; a cap that openably and closeably covers an upper portion of the main body; and a replacement member that is separate from the main body and the cap, and is to be detachably mounted in the recess of the main body in a state of being separated from the cap advance when the nebulizer is to be used, wherein the replacement member includes a film mesh portion that is to oppose the vibration surface, a bottom surface portion to support a circumferential edge of the mesh portion, and a side wall portion that is continuous with an outer edge of the bottom plate portion and is to oppose a side surface of the recess, and when the replacement member is detachably mounted in the recess of the main body in a state of being separated from the cap in advance when the nebulizer is to be used, and the cap is closed with respect to the main body, a protrusion portion protruding toward the main body side of the cap presses the bottom plate portion of the replacement member toward the bottom surface of the recess, and positions the replacement member in a vertical axis direction of the main body.

In the present specification, a "film mesh portion" means an element that has multiple through holes penetrating a film and that nebulizes a liquid by passing the liquid through the through holes.

The planar shape of the recess widely encompasses a ring shape, such as a circle or a rounded-corner rectangle (a rectangle with rounded corners).

The "vertical axis direction" of the main body means the approximate vertical direction.

A user attempting to use the mesh nebulizer according to a preferred embodiment of the present invention detachably mounts the replacement member including the mesh portion, in a state of being separated from the cap, in the recess having the shape that opens toward the top of the main body, in a state in which the cap is open with respect to the main body. Accordingly, the bottom plate portion of the replacement member, which supports the circumferential edge of the mesh portion, opposes the bottom surface of the recess, and the side wall portion of the replacement member opposes the side surface of the recess. In the mounted state, the user closes the cap with respect to the main body. Upon doing so, the protruding portion that protrudes toward the main body side of the cap presses the bottom plate portion of the replacement member toward the bottom surface of the recess, and positions the replacement member in the vertical axis direction of the main body. Accordingly, the mesh portion of the replacement member is positioned with respect to and opposes the vibrating surface of the vibration portion arranged at a position corresponding to the bottom surface of the recess. In this manner, the mesh nebulizer is easily assembled (this state is called the assembled state).

During use, a liquid supply portion supplies the liquid onto the vibration surface of the vibration portion. Accordingly, the liquid is supplied between the vibration surface and the mesh portion. Also, the drive voltage is applied to the vibration portion and the vibration surface is vibrated. Accordingly, the liquid is nebulized and ejected through the mesh portion (or more accurately, through the multiple through holes penetrating the film).

After use, the user opens the cap with respect to the main body and removes the replacement member, which is separated from the cap, from the recess. The above-described replacement member is typically disposed of after use. In this case, the user does not need to clean, disinfect, and dry the replacement member including the mesh portion. Accordingly, maintenance is easy for the user. Also, since the replacement member is completely separate from the cap, it can be manufactured with a relatively small size and low cost. Accordingly, the cost burden for the replacement member is small for the user.

With a mesh nebulizer according to a preferred embodiment of the present invention, the side surface of the recess of the main body increasingly opens toward the top, and the side wall portion of the replacement member increasingly opens toward the top so as to correspond to the side surface of the recess of the main body.

With the mesh nebulizer of this preferred embodiment, the side surface of the recess of the main body increasingly opens toward the top. Accordingly, when mounting the replacement member, if the user places the replacement member in the periphery of the recess, the side wall portion of the replacement member is guided by the side surface of the recess, the bottom plate portion of the replacement member (supports the circumferential edge of the mesh portion) opposes the bottom surface of the recess, and the side wall portion of the replacement member opposes the side surface of the recess. Accordingly, the user can easily mount the replacement member in the recess of the main body.

With a mesh nebulizer according to a preferred embodiment of the present invention, the replacement member includes a finger grip portion that is continuous with an upper edge of the side wall portion and extends radially in a specific direction in the periphery of the center of the side wall portion.

With the mesh nebulizer of this preferred embodiment, when mounting the replacement member, by holding the above-described finger grip portion with his or her hand (e.g., holding it with the thumb and index finger), the user can easily mount the replacement member in the recess of the main body without touching the mesh portion of the replacement member with a finger. Also, after use, the user can easily remove the replacement member from the recess by holding the finger grip portion with his or her hand (e.g., gripping it with the thumb and index finger).

With a mesh nebulizer according to a preferred embodiment of the present invention, the finger grip portion extends in mutually opposite directions in the periphery of the center of the side wall portion.

With the mesh nebulizer of this preferred embodiment, when the replacement member is attached, the user grips the portions of the finger grip portion that extend in mutually opposite directions with his or her hand (e.g., the thumb and index finger) toward the center from both sides (outer sides), such that the user can easily mount the replacement member in the recess of the main body without touching the mesh portion of the replacement member with a finger. In particular, when mounting the replacement member, if mounting is performed in a state in which another portion of the hand (e.g., the pinky, palm, or the like) with which the user holds the finger grip portion of the replacement member is in contact with the side surface or the like of the main member, it is possible to easily reduce or prevent positional misalignment (shaking) of the hand with respect to the main body. Accordingly, the user can more easily mount the replacement member in the recess of the main body. Also, after use, the user can easily remove the replacement member from the recess by gripping the portions of the finger grip portion that extend in mutually opposite directions with his or her hand (e.g., the thumb and index finger) toward the center from both sides (outer sides).

With a mesh nebulizer according to a preferred embodiment of the present invention, a groove that extends radially in a specific direction from the recess is provided in the periphery of the upper edge of the recess of the main body so as to correspond to the finger grip portion of the replacement member.

With the mesh nebulizer of this preferred embodiment, when mounting the replacement member, the user can position the replacement member in the circumferential direction with respect to the recess by aligning the finger grip portion of the replacement member with the groove in the periphery of the upper edge of the recess.

With a mesh nebulizer according to a preferred embodiment of the present invention, the vibration surface is orthogonal or substantially orthogonal to the vertical axis direction of the main body, the bottom surface of the recess of the main body is inclined with respect to the vertical axis direction of the main body, and the mesh portion and the bottom plate portion of the replacement member are inclined with respect to the center of the side wall portion so as to correspond to the bottom surface of the recess of the main body.

With the mesh nebulizer of this preferred embodiment, the bottom surface of the recess of the main body is inclined with respect to the vertical axis direction of the main body and the mesh portion and the bottom plate portion of the replacement member are inclined with respect to the center of the side wall portion such that they correspond to the bottom surface of the recess of the main body. Accordingly, when mounting the replacement member, if the user places the replacement member in the periphery of the recess, the mesh portion and the bottom plate portion of the replacement member are guided so as to correspond to the bottom surface of the recess of the main body. Accordingly, the positioning in the circumferential direction and vertical axis direction of the replacement member with respect to the recess is aided. Also, in the assembled state, the mesh portion is inclined with respect to and opposes the vibration surface. Accordingly, during use, the portion of the mesh portion having a gap that is suitable for the vibration surface functions, such that nebulization of the liquid is performed effectively.

With a mesh nebulizer according to a preferred embodiment of the present invention, a gasket is provided on the side surface of the recess of the main body so as to surround and be in contact with the side wall portion of the replacement member in a circumferential direction.

With the mesh nebulizer of this preferred embodiment, a gasket is provided on the side surface of the recess of the main body so as to surround and be in contact with the side wall portion of the replacement member in the circumferential direction. Accordingly, due to the gasket, during use, the liquid supplied between the vibration surface and the mesh portion can be prevented from overflowing to the outside through the gap between the side surface of the recess and the side wall portion of the replacement member.

With a mesh nebulizer according to a preferred embodiment of the present invention, the replacement member is made of synthetic resin.

With the mesh nebulizer of this preferred embodiment, the replacement member is made of synthetic resin. Accordingly, the replacement member can be manufactured at a low cost.

With a mesh nebulizer according to a preferred embodiment of the present invention, the cap is coupled to the main body via a hinge so as to be able to rotate.

With the mesh nebulizer of this preferred embodiment, the cap is coupled to the main body via a hinge so as to be able to rotate. Accordingly, the user can easily open and close the cap with respect to the main body. Also, the cap will not be lost.

In another aspect, a replacement member according to a preferred embodiment of the present invention included in a mesh nebulizer according to one of the above-described preferred embodiments of the present invention, the replacement member including a film mesh portion that is to oppose the vibration surface; a bottom surface portion to support a circumferential edge of the mesh portion; and a side wall portion that is continuous with an outer edge of the bottom wall portion and is to oppose a side surface of the recess.

After being used in the mesh nebulizer, the replacement member according to this preferred embodiment is typically disposed of. In this case, the user does not need to clean, disinfect, and dry the replacement member including the mesh portion. Accordingly, maintenance is easy for the user. Also, since the replacement member is formed separately from the main body and the cap, it can be manufactured with a relatively small size and low cost. Accordingly, the cost burden for the replacement member is small for the user.

A replacement member according to a preferred embodiment of the present invention includes a finger grip portion that is continuous with the upper edge of the side wall portion and extends radially in a specific direction in the periphery of the center of the side wall portion.

When mounting the replacement member of this preferred embodiment, by holding the above-described finger grip portion with his or her hand (e.g., gripping it with the thumb and index finger), the user can easily mount the replacement member in the recess of the main body without touching the mesh portion of the replacement member with a finger. Also, after use, the user can easily remove the replacement member from the recess by holding the finger grip portion with his or her hand (e.g., gripping it with the thumb and index finger).

With a replacement member according to a preferred embodiment of the present invention, the finger grip portion extends in mutually opposite directions in the periphery of the center of the side wall portion.

When mounting the replacement member of this preferred embodiment, the user grips the portions of the finger grip portion that extend in mutually opposite directions with his or her hand (e.g., the thumb and index finger) toward the center from both sides (outer sides), such that the user can easily mount the replacement member in the recess of the main body without touching the mesh portion of the replacement member with a finger. In particular, when mounting the replacement member, if mounting is performed in a state in which another portion of the hand (e.g., the pinky, palm, or the like) with which the user holds the finger grip portion of the replacement member is in contact with the side surface or the like of the main member, it is possible to easily suppress positional misalignment (shaking) or the hand with respect to the main body. Accordingly, the user can more easily mount the replacement member in the recess of the main body. Also, after use, the user can easily remove the replacement member from the recess by gripping the portions of the finger grip portion that extend in mutually opposite directions with his or her hand (e.g., the thumb and index finger) toward the center from both sides (outer sides).

As is evident from the description above, with the mesh nebulizers according to preferred embodiments of the present invention, maintenance is easy for the user, and the cost burden for the replacement member is small.

Also, the replacement members according to preferred embodiments of the present invention can be manufactured with a relatively small size and low cost. Accordingly, the cost burden for the replacement member is small for the user.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 5A is a diagram showing a view from the right side of a state (assembled state) in which the mesh nebulizer is assembled. FIG. 5B is a diagram showing a view from the front of the mesh nebulizer shown in FIG. 5A, and FIG. 5C is a diagram showing a view from above of the mesh nebulizer shown in FIG. 5A.

FIG. 8A is a plan view showing the replacement member. FIG. 8B is a diagram showing a view from the left side in FIG. 8A of the replacement member, FIG. 8C is a diagram showing a view from the right side in FIG. 8A of the replacement member, and FIG. 8D is a diagram showing a view from the lower side in FIG. 8A of the replacement member. FIG. 8E is a diagram showing a cross-section taken along line VIIIE-VIIIE in FIG. 8A and viewed in the direction of arrows. FIG. 8F is an enlarged view of the vicinity of the mesh portion shown in FIG. 8A.

FIG. 12A is a plan view showing the replacement member of the first modified example. FIG. 12B is a diagram showing a view from the left side in FIG. 12A of the replacement member of the first modified example, FIG. 12C is a diagram showing a view from the right side in FIG. 12A of the replacement member of the first modified example, and FIG. 12D is a diagram showing a view from the lower side in FIG. 12A of the replacement member of the first modified example. FIG. 12E is a diagram showing a cross-section taken along line XIIE-XIIE in FIG. 12A and viewed in the direction of arrows.

FIG. 13A is a plan view showing a replacement member of a second modified example. FIG. 13B is a diagram showing a schematic cross-section viewed from the right side in FIG. 13A of the replacement member of the second modified example of a preferred embodiment of the present invention.

FIG. 14A is a plan view showing a replacement member of a third modified example of a preferred embodiment of the present invention. FIG. 14B is a diagram showing a schematic cross-section viewed from the right side in FIG. 14A of the replacement member of the third modified example.

FIG. 15A is a plan view showing a replacement member of a fourth modified example. FIG. 15B is a diagram showing a schematic cross-section viewed from the right side in FIG. 15A of the replacement member of the fourth modified example, and FIG. 15C is a diagram showing a schematic cross-section viewed from the lower side in FIG. 15A of the replacement member of the fourth modified example.

DETAILED DESCRIPTION OF THE PREFERRED EMBODIMENTS

Hereinafter, preferred embodiments of the present invention will be described in detail with reference to the drawings.

Figure 1:
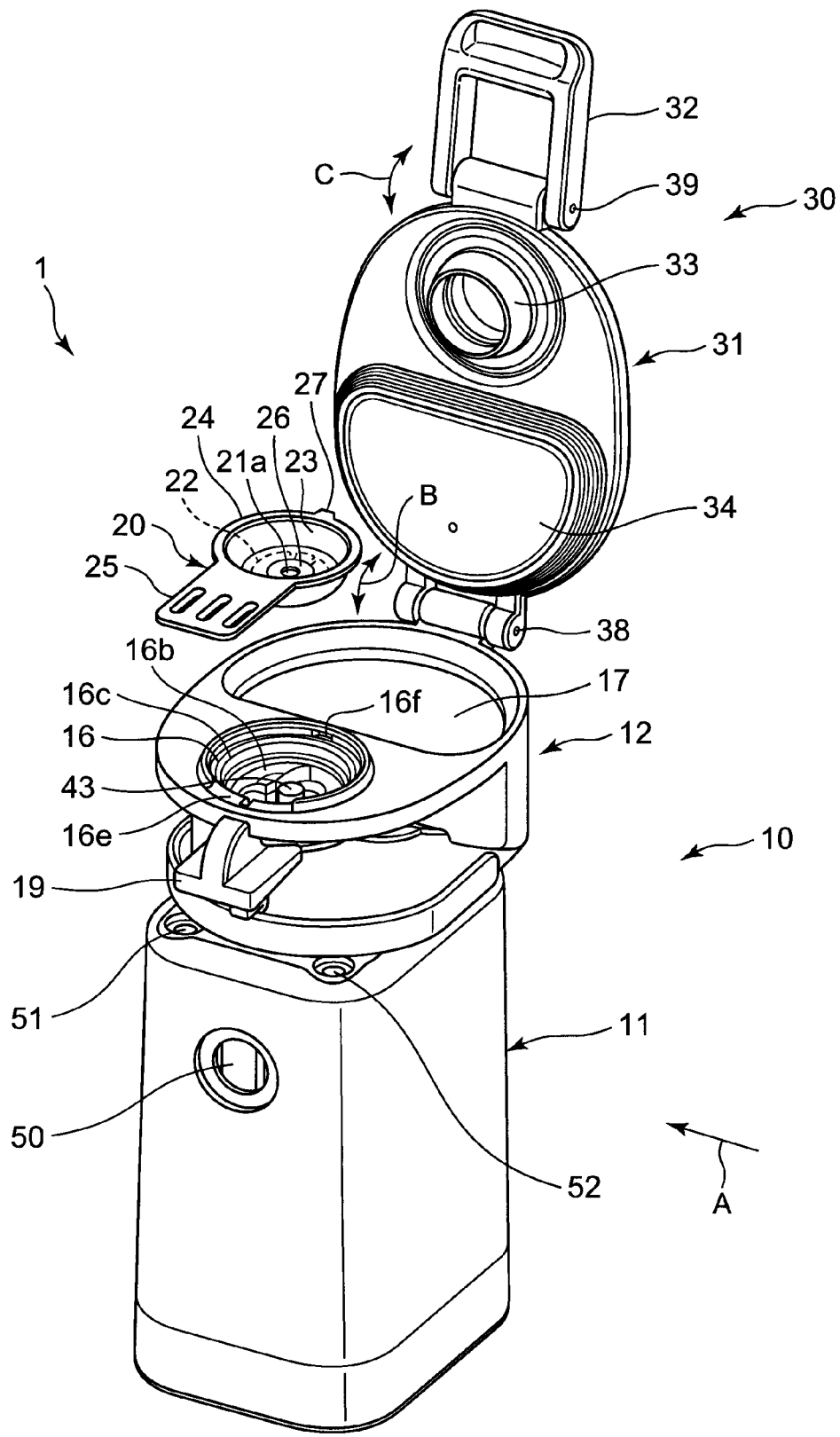
FIG. 1 is a perspective view showing a mesh nebulizer of a preferred embodiment of the present invention in a disassembled state.
Figure 2:
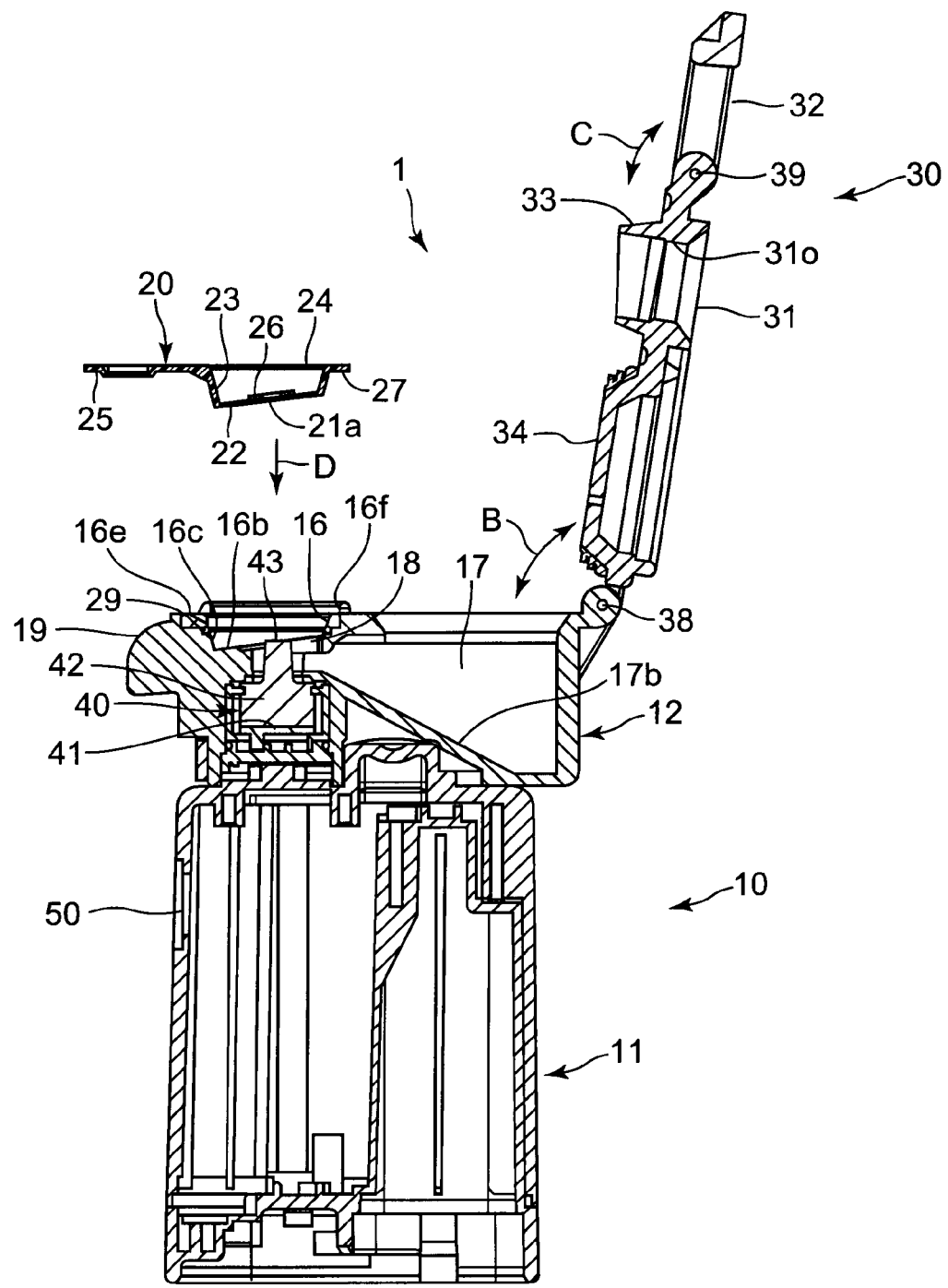
FIG. 2 is a diagram showing a vertical cross-section taken when the mesh nebulizer in the disassembled state shown in FIG. 1 is viewed from the right side.

FIG. 1 shows a perspective view of a mesh nebulizer (indicated overall by reference numeral 1) of a preferred embodiment of the present invention in a disassembled state. FIG. 2 is a diagram showing a vertical cross-section taken when the mesh nebulizer in the disassembled state shown in FIG. 1 is viewed from the right side (direction indicated by arrow A in FIG. 1).

As shown in FIGS. 1 and 2, the mesh nebulizer 1 includes a main body lower portion 11 that has an approximately quadrangular prism external shape, and a main body upper portion 12 that has an approximately elliptical prism outer shape and is detachably mounted on and fit into the main body lower portion 11 from above. The main body lower portion 11 and the main body upper portion 12 define a main body 10.

As shown in FIG. 1, a power source switch 50 to turn on and off the power source of the nebulizer 1 is provided on the front surface of the main body lower portion 11. Also, LED lamps 51 and 52 to perform notification of the operation state of the nebulizer 1 are provided at the upper left corner and upper right corner of the front surface side of the upper surface of the main body lower portion 11. A later-described control system is mainly mounted inside of the main body lower portion 11.

A recess 16 that has an approximately circular planar shape and is opened upward so as to receive a later-described replacement member 20 is provided on the region of the front half of the upper surface of the main body upper portion 12. As can be understood from FIG. 2, the recess 16 includes a bottom surface 16b that is inclined with respect to the vertical axis direction (vertical direction) of the main body 10 and a side surface 16c that increasingly opens toward the top. Also, as can be understood from FIG. 1, a groove 16e that extends radially toward a predetermined direction (in this example, toward the front side) from the recess 16 so as to correspond to a finger grip portion 25 of the later-described replacement member 20 is provided in the periphery of the upper edge of the recess 16. Furthermore, a groove 16f that extends radially to the rear surface side in this example from the recess 16 is provided in the periphery of the upper edge of the recess 16 so as to correspond to a leading end protrusion 27 of the later-described replacement member 20. Furthermore, as shown in FIG. 2, a gasket 29 is provided on the side surface 16c of the recess 16 of the main body 10 so as to surround and be in contact with the side wall portion 23 of the later-described replacement member 20 in the circumferential direction.

A vibration portion 40 is provided at a position corresponding to the recess 16 in the inner portion of the main body upper portion 12. The vibration portion 40 includes an ultrasonic vibrator 41 arranged at a position separated downward from the recess 16, a vibration surface 43 arranged horizontally at a position corresponding to the bottom surface 16b of the recess 16, and a horn 42 that is arranged between the ultrasonic vibrator 41 and the vibration surface 43, amplifies the vibration of the ultrasonic vibrator 41, and transmits the vibration to the vibration surface 43. The drive voltage for the ultrasonic vibrator 41 is supplied from the main body lower portion 11 via a contact electrode provided between the main body upper portion 12 and the main body lower portion 11.

Also, as shown in FIG. 1, a liquid storage portion 17 having an approximately semicircular planar shape is provided in a region on the rear half of the upper surface of the main body upper portion 12. As can be understood from FIG. 2, the liquid storage portion 17 includes the bottom surface 17b, which increasingly gets shallower toward the front surface. Also, a liquid supply path 18 is provided which is continuous with the front surface-side portion of the liquid storage portion 17 and supplies liquid (medicinal liquid) onto the vibration surface 43 of the vibration portion 40 from the liquid storage portion 17. The liquid storage portion 17 and the liquid supply path 18 define a liquid supply portion. In the disassembled state shown in FIGS. 1 and 2, the liquid storage portion 17 is open upward. Accordingly, the user can insert the medicinal liquid into the liquid storage portion 17 from above.

A cover 31 with an approximately elliptical plate shape is coupled to the edge of the rear surface side of the upper surface of the main body upper portion 12 such that it can rotate as indicated by arrow B via a hinge 38 with respect to the main body upper portion 12. On a side opposing the upper surface of the main body upper portion 12, the cover 31 includes a protrusion portion 33 having a shape that protrudes in an approximately cylindrical shape, and a mesa portion 34 having an approximately semicircular planar shape corresponding to the planar shape of the liquid storage portion 17. As will be described later, in the state in which the cover 31 is closed with respect to the main body upper portion 12 and the nebulizer 1 is assembled, the protrusion portion 33 positions the replacement member 20. Also, the mesa portion 34 covers the upper portion of the liquid storage portion 17 and prevents the medicinal liquid from overflowing from the liquid storage portion 17.

Also, an approximately U-shaped engagement frame 32 is coupled to the leading end (the end portion on the side opposite to the hinge 38) of the cover 31 so as to be able to rotate as indicated by arrow C via the hinge 39 with respect to the cover 31. In a state in which the cover 31 is closed with respect to the main body upper portion 12, this engagement frame 32 engages with the engagement protrusion 19 provided on the front surface upper portion of the main body upper portion 12 when rotated toward the front surface of the main body upper portion 12. Accordingly, the cover 31 is able to be fixed in a state of being closed with respect to the main body upper portion 12. The cover 31 and the engagement frame 32 define a cap 30. According to this configuration, the user can easily open and close the cap 30 with respect to the main body 10 (main body upper portion 12). Also, the cap 30 will not be lost.

FIGS. 1 and 2 show the replacement member 20 that is separate from the main body 10 and the cap 30. The replacement member 20 is detachably mounted in the recess 16 of the main body upper portion 12 in a state of being separated from the cap 30 in advance when the nebulizer 1 is to be used.

FIGS. 8A to 8F show the detailed configuration of the replacement member 20. As can be understood from FIGS. 8A and 8E, the replacement member 20 includes a flat film 21 that is to oppose the vibration surface 43 (see FIGS. 1 and 2), an approximately ring-shaped bottom plate portion 22 that supports the circumferential edge of the film 21, a side wall portion 23 that is continuous with the outer edge of the bottom plate portion 22 and is to oppose the side surface 16c (see FIGS. 1 and 2) of the recess 16, and a flange portion 24 that is continuous with the upper edge of the side wall portion 23 and extends radially (toward the outside in the radial direction) in the periphery of the upper edge. The film 21 is attached to the upper surface of the bottom plate portion 22 through adhesion or welding. The region in the approximate center of the film 21 defines the mesh portion 21a.

FIG. 8F is an enlarged view of the vicinity of the mesh portion 21a shown in FIG. 8A. In this example, the mesh portion 21a is defined by providing many through holes (not shown) with a diameter of about 3 μm in a square region in which one side dimension X=1.5 mm, in the film 21 having a thickness of about 30 μm. A flat ring-shaped ring member 26 with a thickness of about 400 μm is attached through adhesion or welding to a position surrounding the mesh portion 21a on the film 21. The ring member 26 is attached in order to keep the mesh portion 21a as flat as possible and to adjust the unique vibration rate of the film 21 including the mesh portion 21a. In this example, the inner diameter dimension ID of the ring member 26 is set to about 2.2 mm, and the outer diameter dimension OD of the ring member 26 is set to about 6.0 mm. The mesh portion 21a is located inside of an opening 26o of the ring member 26 so as to be able to discharge the medicinal liquid nebulized through the above-described through holes.

As can be understood from FIG. 8E, the mesh portion 21a and the bottom plate portion 22 of the replacement member 20 are inclined with respect to the center 23c of the side wall portion 23 so as to correspond to the bottom surface 16b (see FIG. 2) of the recess 16 of the main body 10. Also, the side wall portion 23 of the replacement member 20 increasingly opens toward the top, so as to correspond to the side surface 16c (see FIG. 2) of the recess 16 of the main body 10. Note that a protrusion 22p protrudes inward in the radial direction from the bottom plate portion 22 and stops directly below the ring member 26 in order to keep the film 21 as flat as possible.

Also, as can be understood from FIGS. 8A and 8E, in this replacement member 20, the finger grip portion 25 extends past the flange portion 24 radially in a specific direction (in this example, leftward in FIGS. 8A and 8E) in the periphery of the center 23c of the side wall portion 23. The finger grip portion 25 is provided for ease of gripping the bottom and top with the thumb and index finger, for example, when the user holds the replacement member 20 with his or her hand.

The finger grip portion 25 is provided with bumps 25p for preventing slippage. Furthermore, with this replacement member 20, the leading end protrusion 27 protrudes past the flange portion 24 in a direction opposite to the direction in which the finger grip portion 25 extends, and in this example, rightward in FIGS. 8A and 8E. The finger grip portion 25 and the leading end protrusion 27 enable positioning in the circumferential direction of the replacement member 20 with respect to the recess 16 when the user mounts the replacement member 20 in the recess 16 of the main body upper portion 12.

In this example, all of the elements of the replacement member 20 are made of synthetic resin. Accordingly, the replacement member 20 can be manufactured at a low cost. Examples of the synthetic resin forming the replacement member 20 include polyamide-based resin, polyester, syndio-polystyrene, polysulfone, polyether sulfone, polyether ether ketone, polyether imide, polyamide imide, PPS (polyphenylene sulfide), epoxy, phenol, and polyimide.

Figure 9:
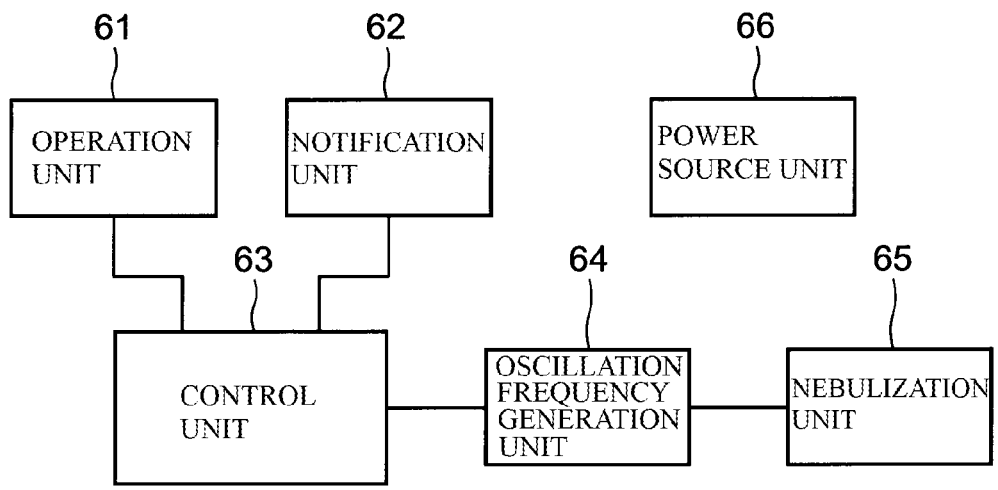
FIG. 9 is a diagram showing a block configuration of a control system mounted in the main body of the mesh nebulizer.
Figure 10:
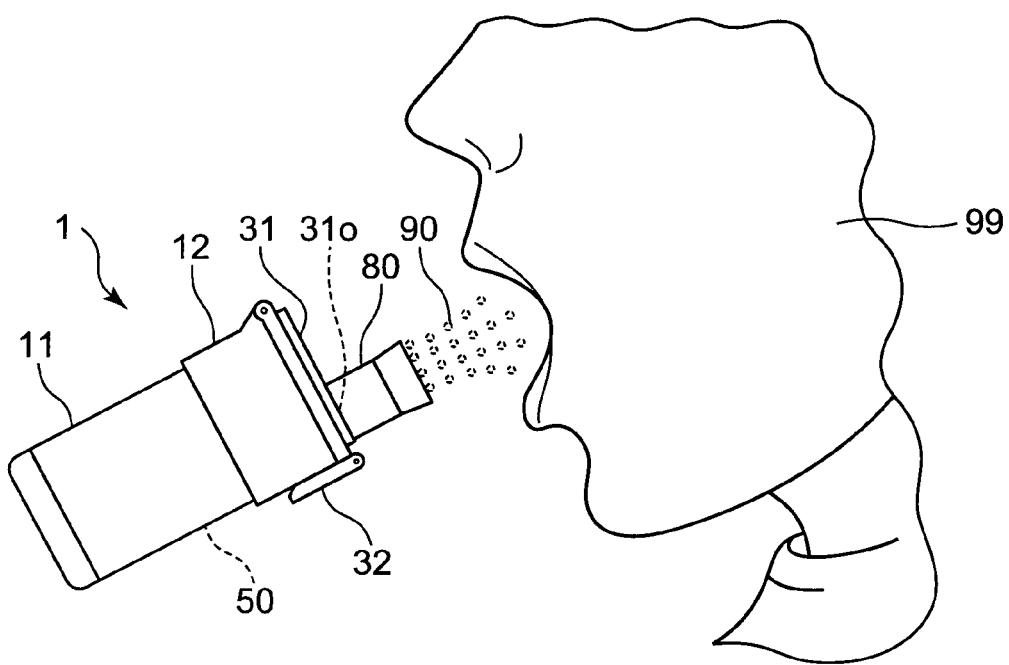
FIG. 10 is a diagram illustrating a mode in which the user uses the mesh nebulizer.

FIG. 9 shows a block configuration of a control system mounted in the main body 10 of the mesh nebulizer 1. The mesh nebulizer 1 is configured or programmed to include an operation unit 61, a notification unit 62, a control unit 63, an oscillation frequency generation unit 64, a nebulization unit 65, and a power source unit 66. In this example, the operation unit 61 includes a power source switch 50 shown in FIG. 1. In this example, the notification unit 62 includes the LED lamps 51 and 52 shown in FIG. 1, and may further include a buzzer (not shown). The oscillation frequency generation unit 64 applies an AC drive voltage to the nebulization unit 65 based on a control signal from the control unit 63. The drive voltage is output over a certain output period after the power source switch 50 is pressed, for example. The output period can also be measured using a timer (not shown). The nebulization unit 65 includes the vibration portion 40 and the mesh portion 21a of the replacement member 20 shown in FIG. 1. The AC drive voltage from the oscillation frequency generation unit 64 is applied to the ultrasonic vibrator 41 of the vibration portion 40 of the nebulization unit 65. The vibration of the ultrasonic vibrator 41 is amplified by the horn 42 and is transmitted to the vibration surface 43. When the vibration surface 43 vibrates, the medicinal liquid supplied to the gap between the vibration surface 43 and the mesh portion 21a is nebulized and ejected through the mesh portion 21a. The control unit 63 includes a CPU (Central Processing Unit), sends a signal to the nebulization unit 65 via the oscillation frequency generation unit 64, and controls the nebulization amount, the continued operation time, and the like. Also, the control unit 63 performs notification of the fact that the power source is on by illuminating the LED lamp 51, performs notification of the fact that the capacity of the battery is insufficient by causing the LED lamp 52 to blink, and the like. The power source unit 66 includes a battery (e.g., a DC3V chargeable/dischargeable secondary battery) and supplies power to the units of the control system.

A user who attempts to use the mesh nebulizer 1 mounts the replacement member 20 having the mesh portion 21a, in a state of being separated from the cap 30, as indicated by arrow D in FIG. 2 in the recess 16 having a shape that opens toward the top of the main body 10 in a state in which the cap 30 is open with respect to the main body 10 as shown in FIGS. 1 and 2.

When mounting the replacement member 20, by holding the finger grip portion 25 with his or her own hand (gripping the finger grip portion 25 from the top and bottom with the thumb and index finger), the user can easily mount the replacement member 20 in the recess 16 of the main body 10 without touching the mesh portion 21*a* of the replacement member 20 with a finger.

Also, when mounting the replacement member 20, the replacement member 20 can be positioned in the circumferential direction with respect to the recess 16 due to the user aligning the leading end protrusion 27 and the finger grip portion 25 of the replacement member 20 with the groove 16*f* and the groove 16*e* in the periphery of the upper edge of the recess 16.

Also, as described above, the side surface 16*c* of the recess 16 of the main body 10 increasingly opens toward the top. Also, the side wall portion 23 of the replacement member 20 increasingly opens toward the top, so as to correspond to the side surface 16*c* (see FIG. 2) of the recess 16 of the main body 10. Accordingly, when mounting the replacement member 20, if the user places the replacement member 20 in the periphery of the recess 16, the side wall portion 23 of the replacement member 20 is guided downward by the side wall 16*c* of the recess 16.

Also, the bottom surface 16*b* of the recess 16 of the main body 10 is inclined with respect to the vertical axis direction (vertical direction) of the main body 10, and the mesh portion 21*a* and the bottom plate portion 22 of the replacement member 20 are inclined with respect to the center 23*c* of the side wall portion 23 so as to correspond to the bottom surface 16*b* of the recess 16 of the main body 10. Accordingly, when mounting the replacement member 20, if the user places the replacement member 20 in the periphery of the recess 16, the mesh portion 21*a* and the bottom plate portion 22 of the replacement member 20 are guided so as to correspond to the bottom surface 16*b* of the recess 16 of the main body 10. Accordingly, positioning in the circumferential direction and the vertical axis direction of the replacement member 20 with respect to the recess 16 is aided.

Figure 3:
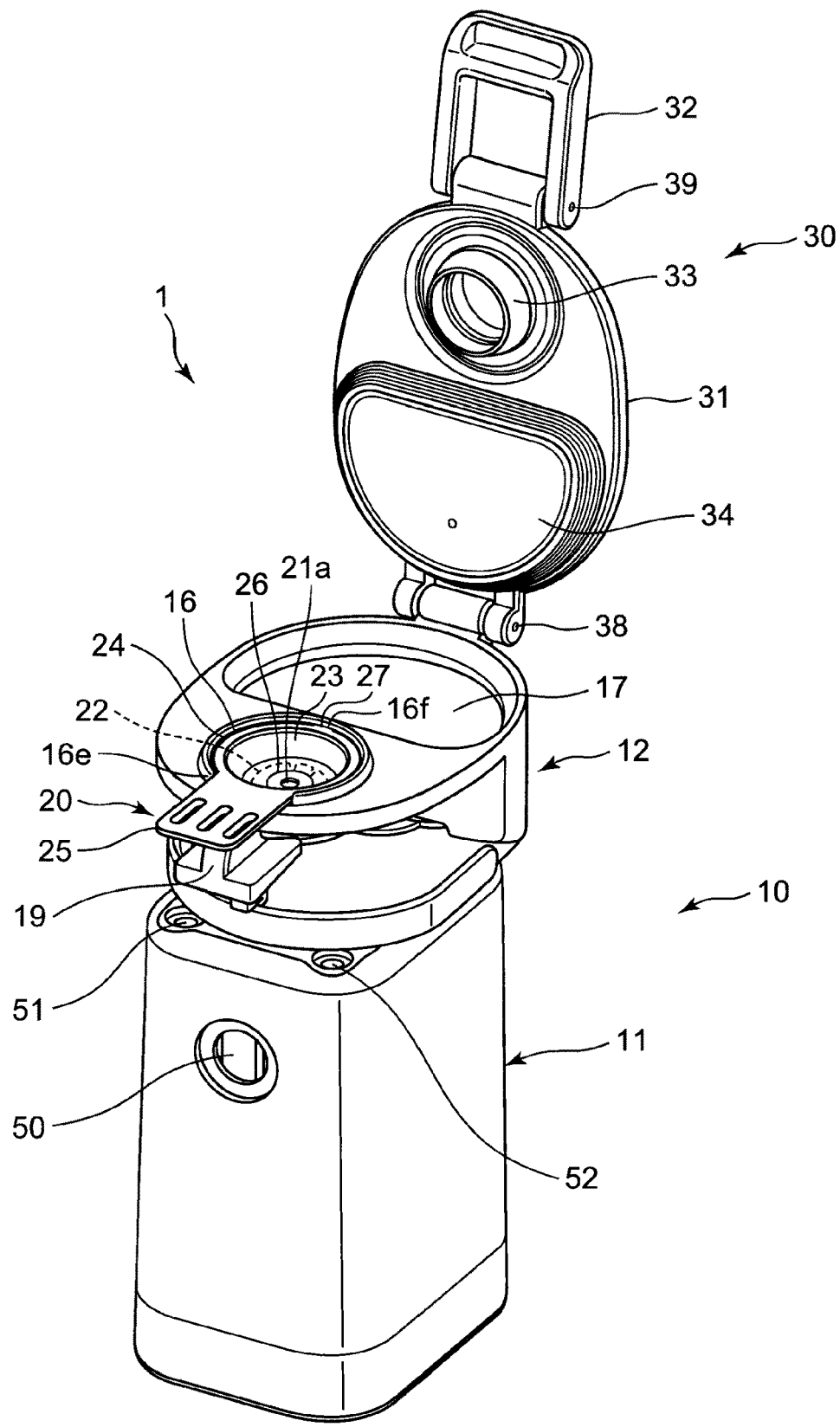
FIG. 3 is a perspective view showing a state (mounted state) in which a replacement member including a mesh portion is mounted in the mesh nebulizer.
Figure 4:
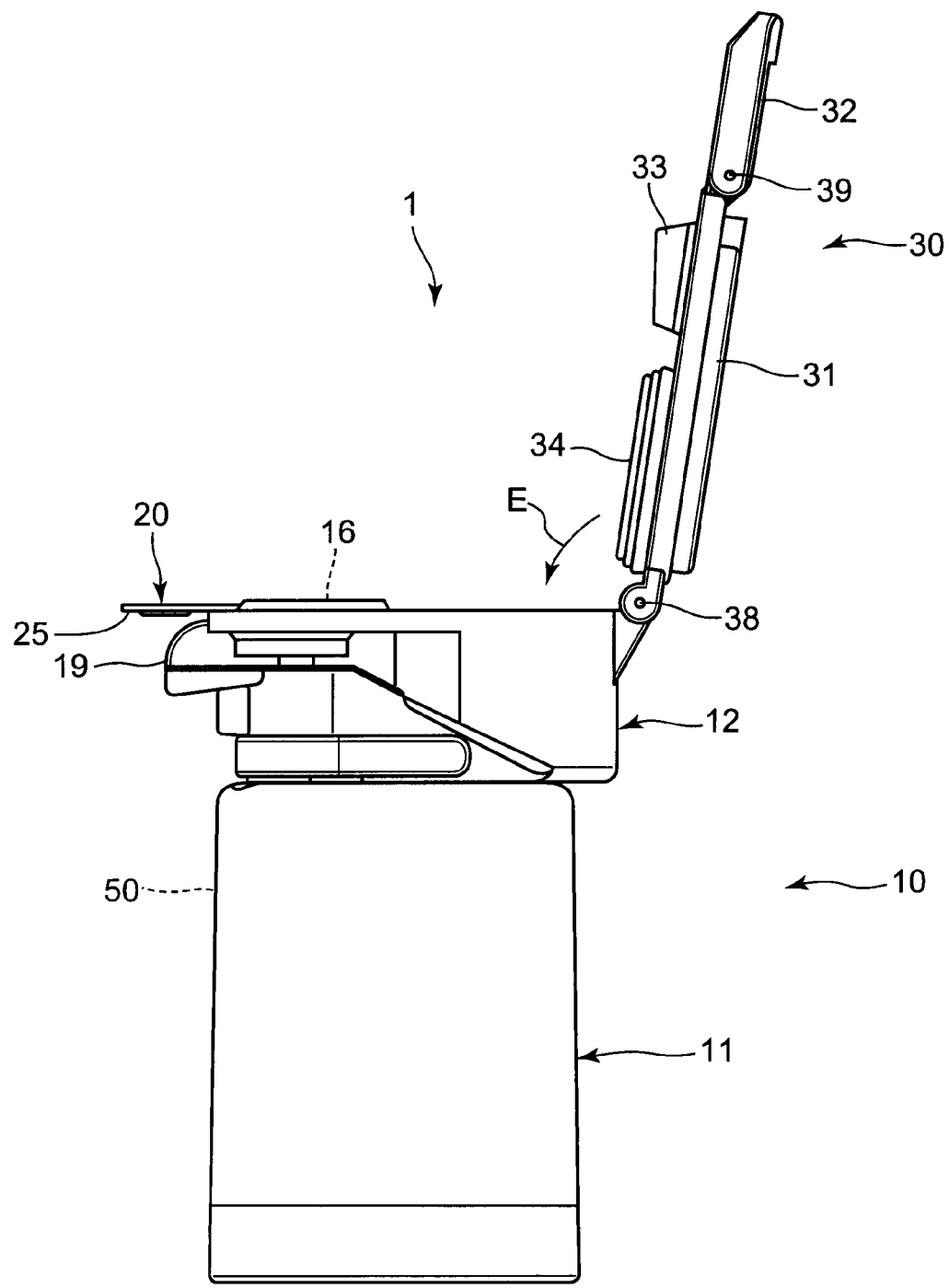
FIG. 4 is a diagram showing a view from the right side of the mesh nebulizer in the mounted state shown in FIG. 3.
Figure 6:
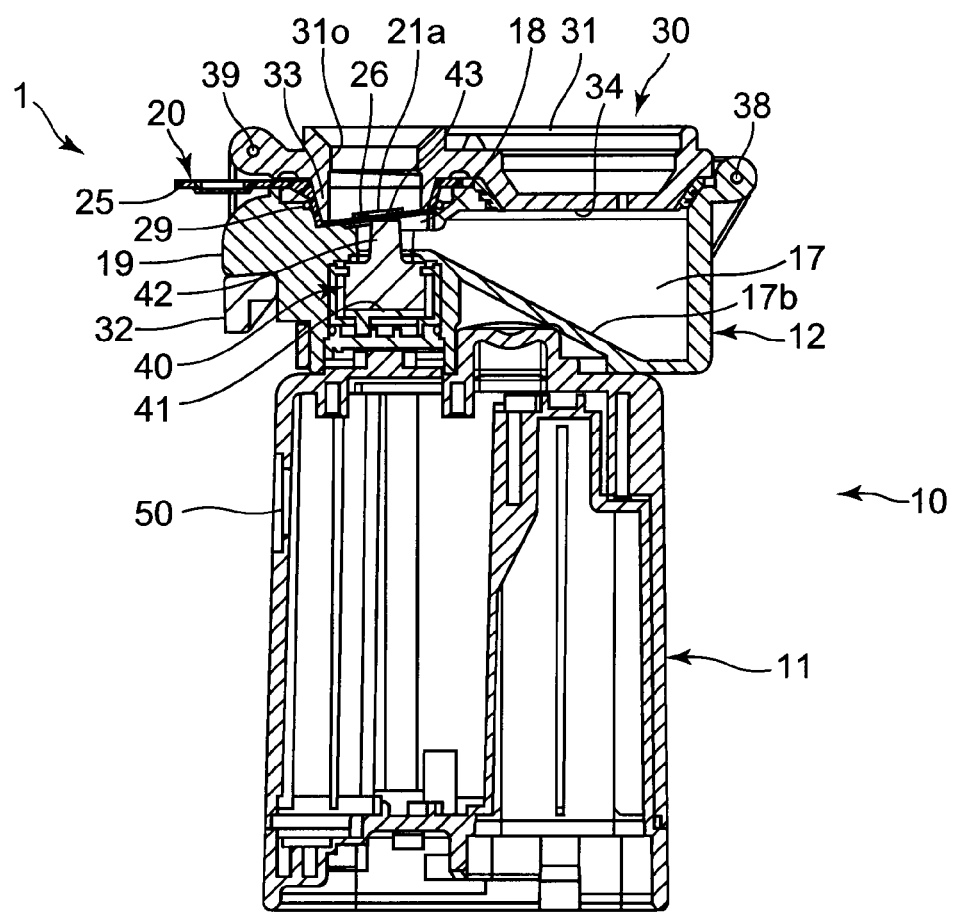
FIG. 6 is a diagram showing a vertical cross-section taken when the mesh nebulizer in the assembled state is viewed from the right side.
Figure 7:
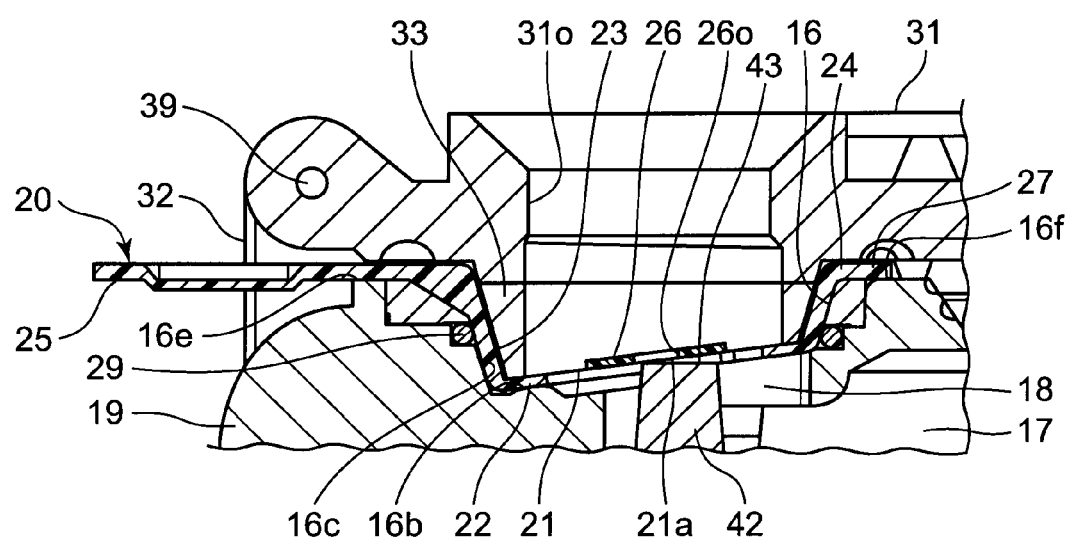
FIG. 7 is an enlarged view of the vicinity of the replacement member shown in FIG. 6.

Accordingly, as shown in FIGS. 3 and 4, the bottom plate portion 22 of the replacement member 20, which supports the circumferential edge of the mesh portion 21*a*, opposes the bottom surface 16*b* of the recess 16, and the side wall portion 23 of the replacement member 20 opposes the side wall 16*c* of the recess 16. Accordingly, the user can easily mount the replacement member 20 in the recess 16 of the main body 10 in a state of being separated from the cap 30. This state is called the mounted state.

In the mounted state, the user closes the cap 30 with respect to the main body 10. Specifically, the user closes the cover 31 with respect to the main body upper portion 12 as indicated by arrow E in FIG. 4. Furthermore, in a state in which the cover 31 is closed with respect to the main body upper portion 12, the user rotates the engagement frame 32 toward the front surface of the main body upper portion 12 as indicated by arrow F in FIG. 5A. Upon doing so, the engagement frame 32 moves past the finger grip portion 25 of the replacement member 20 and engages with the engagement protrusion 19 provided on the upper portion of the front surface of the main body upper portion 12. Accordingly, the cover 31 is fixed in a state of being closed with respect to the main body upper portion 12. In this manner, the mesh nebulizer 1 is easily assembled. This state is called the assembled state. Note that FIG. 5B is a diagram showing a view from the front of the mesh nebulizer 1 shown in FIG. 5A, and FIG. 5C is a diagram showing a view from above of the mesh nebulizer 1 shown in FIG. 5A. Also, FIG. 6A shows a vertical cross-section in a view from the right side of the mesh nebulizer 1 in the assembled state.

In the assembled state, the mesa portion 34 of the cover 31 closes the upper portion of the liquid storage portion 17 and prevents the medicinal liquid from overflowing from the liquid storage portion 17. Also, as can be understood from FIG. 7 (enlarged view of the vicinity of the replacement member 20 in FIG. 6), in the assembled state, the protrusion portion 33 provided protruding toward the main body upper portion 12 side of the cap 30 presses the bottom plate portion 22 of the replacement member 20 toward the bottom surface 16*b* of the recess 16 and positions the replacement member 20 in the vertical axis direction of the main body 10. Accordingly, the mesh portion 21*a* of the replacement member 20 is positioned facing the vibration surface 43 of the vibration portion 40 arranged at a position corresponding to the bottom surface 16*b* of the recess 16.

Also, in the assembled state, the mesh portion 21*a* is inclined with respect to and opposes the vibration surface 43. Accordingly, during use, which will be described next, the portion of the mesh portion 21*a* having a suitable gap with respect to the vibration surface 43 functions, and nebulization of the medicinal liquid is performed effectively.

Also, as described above, the gasket 29 is provided on the side surface 16*c* of the recess 16 of the main body 10 so as to surround and be in contact with the side wall portion 23 of the replacement member 20 in the circumferential direction. Accordingly, due to the gasket 29, during use, which will be described next, the medicinal liquid supplied between the vibration surface 43 and the mesh portion 21*a* is prevented from overflowing to the outside through the gap between the side surface 16*c* of the recess 16 and the side wall portion 23 of the replacement member 20.

In the case of using the mesh nebulizer 1, the user inserts the medicinal liquid into the liquid storage portion 17 of the main body upper portion 12 in advance. Also, as shown in FIG. 10, in the assembled state, the user detachably attaches a mouthpiece 80, for example, to an opening 31*o* in the protrusion portion 33 of the cover 31. Note that instead of the mouthpiece 80, an inhalation mask that covers the face of a user 99 may be attached.

As shown in FIG. 10, if the user tilts the mesh nebulizer slightly forward, the medicinal liquid is supplied onto the vibration surface 43 of the vibration portion 40 through the liquid supply path 18 from the liquid storage portion 17 forming the liquid supply portion. In other words, medicinal liquid is supplied between the vibration surface 43 and the mesh portion 21*a*. Also, when the user turns on the power source switch 50, the drive voltage is applied to the ultrasonic vibrator 41 of the vibration portion 40 and the vibration surface 43 is vibrated. Accordingly, the medicinal liquid 90 is nebulized and ejected through the mesh portion 21*a* (or more accurately, through the multiple through holes penetrating the film 21).

After using the mesh nebulizer 1, the user removes the mouthpiece 80 and removes the main body upper portion 12 from the main body lower portion 11. Also, the cap 30 is opened with respect to the main body upper portion 12 and the replacement member 20, which is separated from the cap 30, is removed from the recess 16. At this time, the user 99 can easily remove the replacement member 20 from the recess 16 by holding the finger grip portion 25 in his or her hand (e.g., by gripping the top and bottom of the finger grip portion 25 with the thumb and index finger).

The user discharges the medicinal liquid remaining in the liquid storage portion 17 by tilting the main body upper portion 12. Also, the user washes, disinfects, and dries the mouthpiece 80 and the main body upper portion 12. The main body lower portion 11 is also washed, disinfected, and dried as needed.

The replacement member 20 is typically disposed of after use. In this case, the user does not need to clean, disinfect, and dry the replacement member 20 including the mesh portion 21a. Accordingly, maintenance is easy for the user. Also, the replacement member 20 is formed separated from the main body 10 and the cap 30 and is made of synthetic resin, and therefore can be manufactured with a relatively small size and low cost. Accordingly, the cost burden for the replacement member 20 is small for the user.

Figure 11:
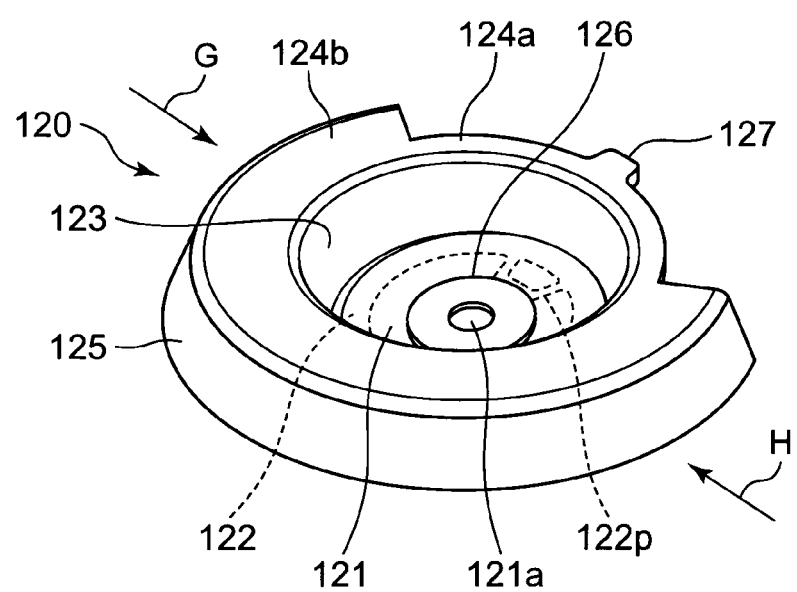
FIG. 11 is a perspective view showing a replacement member of a first modified example of a preferred embodiment of the present invention.

FIG. 11 shows a perspective view of a replacement member 120 of a first modified example of a preferred embodiment of the present invention, which corresponds to the replacement member 20 shown in FIG. 1. Also, FIGS. 12A to 12E show the replacement member 120 of the first modified example, in correspondence with FIGS. 8A to 8E. In FIGS. 11 and 12A to 12E, the reference numerals indicating the elements of the replacement member 120 is obtained by adding 100 to the reference numerals indicating the corresponding elements of the replacement member 20. Description of the replacement member 120 that is redundant with that of the replacement member 20 will be omitted unless otherwise stated.

As can be understood from FIG. 12A, with this replacement member 120, the flange portion that is continuous with the upper edge of the side wall portion 123 is divided into two portions 124a and 124b in the periphery of the center 123c of the side wall portion 123. In FIG. 12A, the flange portion 124a takes up an approximately 120-degree angle range in a view from the center 123c of the side wall portion 123 on a side (right side) of the leading end protrusion 127, and extends radially. The flange portion 124b takes up an approximately 240-degree angle range excluding the flange portion 124a in a view from the center 123c of the side wall portion 123 and extends radially. The radial direction dimension of the flange portion 124b is set to be larger than the radial direction dimension of the flange portion 124a.

With the replacement member 120, instead of the finger grip portion 25 of the replacement member 20, a skirt portion 125 serving as a finger grip portion is provided continuous with the outer edge of the flange portion 124b. This skirt portion 125 increasingly opens toward the bottom, as with the side surface of a circular cone, and stops approximately at the height of the bottom plate portion 122. In the periphery of the center 123c of the side wall portion 123, the angle region of the skirt portion 125 takes up approximately 240 degrees, similarly to the angle region of the flange portion 124b.

When mounting the replacement member 120, the user grips the portions of the skirt portion 125 that extend in mutually opposite directions with his or her own hand (e.g., with the thumb and index finger), toward the center from both sides (outer sides) as indicated by arrows G and H in FIG. 11, for example, and thus the user can easily mount the replacement member 120 in the recess 16 of the main body upper portion 12 without touching the mesh portion 121a of the replacement member 120 with a finger. In particular, when mounting the replacement member 120, if the user performs mounting in a state in which another portion of the hand (e.g., the pinky, palm, or the like) holding the skirt portion 125 of the replacement member 120 comes into contact with the side surface of the main body 10 or the like, positional misalignment (shaking) of the hand with respect to the main body 10 can be easily suppressed. Accordingly, the user can more easily mount the replacement member 120 in the recess 16 of the main body upper portion 12. Also, after use, the user can easily remove the replacement member 120 from the recess 16 by pinching the portions of the skirt portion 125 extending in mutually opposite directions with his or her hand (e.g., the thumb and index finger), toward the center from both sides (outer sides).

Note that in this example, the groove 16e in the periphery of the upper edge of the recess 16 of the main body upper portion 12 is provided so as to correspond to the skirt portion 125.

FIG. 13A shows a view from above of a replacement member 220 of a second modified example of a preferred embodiment of the present invention. FIG. 13B shows a schematic cross-section taken when the replacement member 220 is viewed from the right side in FIG. 13A (for the sake of simplicity, the specific configuration of the vicinity of the mesh portion 221a is omitted and is indicated by a two-dot chain line). In FIGS. 13A and 13B, the reference numerals indicating the elements of the replacement members 220 are obtained by adding 200 to the reference numerals indicating the corresponding elements of the replacement member 20. Description of the replacement member 220 that is redundant with that of the replacement member 20 will be omitted unless otherwise stated.

In this replacement member 220, a protrusion 223p protrudes inward in the radial direction from a side wall portion 223 so as to come into contact with the upper surface of the ring member 226. The upper surface of the ring member 226 is pressed down by the protrusion 223p. Accordingly, the film 21 can be kept as flat as possible. In regard to this point, a protrusion 323p of a replacement member 320 of a later-described third modified example, a protrusion 423p of a replacement member 420 of a fourth modified example, and a protrusion 523p of a replacement member 520 of a fifth modified example are also constituted similarly and exhibit similar effects.

Note that in this replacement member 220, the element corresponding to the leading end protrusion 27 in the replacement member 20 has been omitted. The later-described replacement members 320, 420, and 520 are also similar in this regard as well.

FIG. 14A shows a view from above of a replacement member 320 of a third modified example of a preferred embodiment of the present invention. FIG. 14B shows a schematic cross-section taken when the replacement member 320 is viewed from the right side in FIG. 14A (for the sake of simplicity, the specific configuration of the vicinity of the mesh portion 321a is omitted and is indicated by a two-dot chain line). In FIGS. 14A and 14B, the reference numerals indicating the elements of the replacement members 320 are obtained by adding 300 to the reference numerals indicating the corresponding elements of the replacement member 20. Description of the replacement member 320 that is redundant with that of the replacement member 20 will be omitted unless otherwise stated.

With this replacement member 320, the angle range taken up by a finger grip portion 325 is expanded around the center of a side wall portion 323 with respect to the replacement member 20, and is set to about 270 degrees. Accordingly, when the replacement member 320 is mounted in or detached from the recess 16 of the main body upper portion 12, the angle range in which the user can hold the finger grip portion 325 of the replacement member 320 is wider around the center of the side wall portion 323, and thus mounting and detaching are easier.

Note that in this example, the groove 16e in the periphery of the upper edge of the recess 16 of the main body upper portion 12 is provided so as to correspond to the finger grip portion 325.

FIG. 15A shows a view from above of a replacement member 420 of a fourth modified example of a preferred embodiment of the present invention. FIG. 15B shows a schematic cross-section taken when the replacement member 420 is viewed from the right side in FIG. 15A, and FIG. 15C shows a schematic cross-section taken when the replacement member 420 is viewed from below in FIG. 15A (for the sake of simplicity, the specific configuration of the vicinity of the mesh portion 221a is omitted and is indicated by a two-dot chain line). In FIGS. 15A and 15B, the reference numerals indicating the elements of the replacement members 420 are obtained by adding 400 to the reference numerals indicating the corresponding elements of the replacement member 20. Description of the replacement member 420 that is redundant with that of the replacement member 20 will be omitted unless otherwise stated.

As can be understood from FIG. 15A, with this replacement member 420, the flange portion that is continuous with the upper edge of the side wall portion 423 is divided into four portions 424a, 424b, 424c, and 424d in the periphery of the center of the side wall portion 423. The flange portions 424a and 424d take up an approximately 90-degree angle range in a view from the center of the side wall portion 423 on mutually opposite sides in FIG. 15A, and extend radially. The flange portions 424b and 424c extend leftward and rightward in FIG. 15A in mutually opposite directions from the upper edge of the side wall portion 423. The dimensions in the left-right direction of the flange portions 424b and 424c are set to be larger than the dimensions in the radial direction of the flange portions 424a and 424d.

In this replacement member 420, instead of the finger grip portion 25 of the replacement member 20, skirt portions 425b and 425c serving as finger grip portions are provided continuous with the outer edges of the flange portions 424b and 424c. These skirt portions 425b and 425c extend vertically downward in a flat plate shape, and stop approximately at the height of the bottom plate portion 422.

When mounting the replacement member 420, the user grips the skirt portions 425b and 425c with his or her own hand (e.g., with the thumb and index finger) toward the center from both sides (outer sides), and thereby the user can easily mount the replacement member 420 in the recess 16 of the main body upper portion 12 without touching the mesh portion 421a of the replacement member 420 with a finger. In particular, when mounting the replacement member 420, if the user performs mounting in a state in which another portion of the hand (e.g., the pinky, palm, or the like) holding the skirt portions 425b and 425c of the replacement member 420 comes into contact with the side surface of the main body 10 or the like, positional misalignment (shaking) of the hand with respect to the main body 10 can be easily suppressed. Accordingly, the user can more easily mount the replacement member 120 in the recess 16 of the main body upper portion 42. Also, after use, the user can easily remove the replacement member 420 from the recess 46 by gripping the skirt portions 425b and 425c with his or her hand (e.g., the thumb and index finger) toward the center from both sides (outer sides).

Note that in this example, the groove 16e in the periphery of the upper edge of the recess 16 of the main body upper portion 12 is provided so as to correspond to the skirt portions 425b and 425c.

Figure 16B:
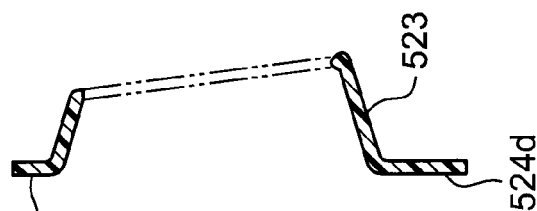
FIG. 16B is a diagram showing a schematic cross-section viewed from the right side in FIG. 16A of the replacement member of the fifth modified example.
Figure 16A:
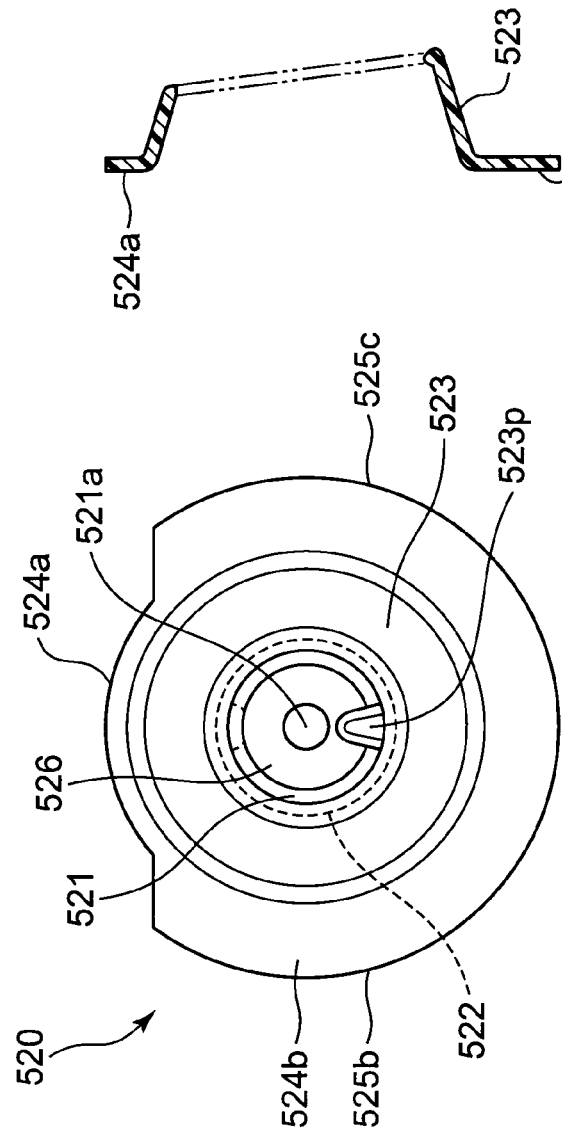
FIG. 16A is a plan view showing a replacement member of a fifth modified example.
Figure 16C:
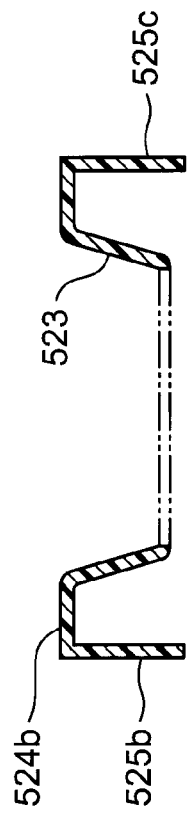
FIG. 16C is a diagram showing a schematic cross-section viewed from the lower side in FIG. 16A of the replacement member of the fifth modified example.

FIG. 16A shows a view from above of a replacement member 520 of a fifth modified example of a preferred embodiment of the present invention. FIG. 16B shows a schematic cross-section taken when the replacement member 520 is viewed from the right side in FIG. 16A, and FIG. 16C shows a schematic cross-section taken when the replacement member 520 is viewed from below in FIG. 16A (for the sake of simplicity, the specific configuration of the vicinity of the mesh portion 521a is omitted and is indicated by a two-dot chain line). In FIGS. 16A and 16B, the reference numerals indicating the elements of the replacement members 520 are obtained by adding 500 to the reference numerals indicating the corresponding elements of the replacement member 20. Description of the replacement member 520 that is redundant with that of the replacement member 20 will be omitted unless otherwise stated.

As can be understood from FIG. 16A, with this replacement member 520, similarly to the flange portion in the replacement member 120 of the first modified example, the flange portion that is continuous with the upper edge of the side wall portion 523 is divided into two portions 524a and 524b around the center of the side wall portion 523. In FIG. 16A, the flange portion 524a takes up an approximately 90-degree angle range in a view from the center of the side wall portion 523 and extends radially. The flange portion 524b takes up an approximately 270-degree angle range excluding the flange portion 524a in a view from the center of the side wall portion 523 and extends radially. The radial direction dimension of the flange portion 524b is set to be larger than the radial direction dimension of the flange portion 524a.

With this replacement member 520, similarly to the flange portion in the replacement member 120 of the first modified example, skirt portions 525b and 525c serving as finger grip portions are provided continuous with the outer edges of only the left side portion and the right side portion in FIG. 16A of the flange portion 524b. These skirt portions 525b and 525c extend downward as with the side surface of a cylinder, and stop approximately at the height of the bottom plate portion 522.

When mounting the replacement member 520, the user grips the skirt portions 525b and 525c with his or her own hand (e.g., with the thumb and index finger) toward the center from both sides (outer sides), and thereby the user can easily mount the replacement member 520 in the recess 16 of the main body upper portion 12 without touching the mesh portion 521a of the replacement member 520 with a finger. In particular, when mounting the replacement member 520, if the user performs mounting in a state in which another portion of the hand (e.g., the pinky, palm, or the like) holding the skirt portion 525 of the replacement member 520 is in contact with the side surface of the main body 10 or the like, positional misalignment (shaking) of the hand with respect to the main body 10 can be easily suppressed. Accordingly, the user can more easily mount the replacement member 520 in the recess 16 of the main body upper portion 12. Also, after use, the user can easily remove the replacement member 520 from the recess 16 by gripping the skirt portions 525b and 525c with his or her hand (e.g., the thumb and index finger) toward the center from both sides (outer sides).

Note that in this example, the groove 16e in the periphery of the upper edge of the recess 16 of the main body upper portion 12 is provided so as to correspond to the skirt portion 525.

In the above-described preferred embodiments, the planar shape of the recess 16 of the main body upper portion 12 is circular. Also, accompanying that, the bottom plate portions of the replacement members 20, 120, 220, 320, 420, and 520, and the planar shape of the side wall portion are circular. However, there is no limitation to this, and the planar shape of the recess 16 may be another ring shape, such as a rounded-corner rectangle (a rectangle with rounded corners). In this case, the bottom plate portions of the replacement members and the planar shape of the side wall portion need only be set to correspond to the planar shape of the recess 16.

The above-described preferred embodiments are illustrative, and various modifications are possible without departing from the scope of the present invention. The above-described multiple preferred embodiments can be established individually, and can be combined together. Also, various characteristics in different preferred embodiments can be established individually, and characteristics in different preferred embodiments can be combined together.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A mesh nebulizer for nebulizing and ejecting a liquid through a mesh portion, the mesh nebulizer comprising:
    a main body including a recess with a shape that is open upward, the main body including a vibration portion with a vibration surface arranged at a position corresponding to a bottom surface of the recess, and a liquid supply portion to supply liquid onto the vibration surface of the vibration portion;
    a cap to openably and closeably cover an upper portion of the main body; and
    a replacement member that is separate from the main body and the cap, and is to be detachably mounted in the recess of the main body in a state of being separated from the cap in advance of when the nebulizer is to be used; wherein
    the replacement member includes a film mesh portion that is to oppose the vibration surface, a bottom surface portion to support a circumferential edge of the mesh portion, and a side wall portion that is continuous with an outer edge of the bottom surface portion and is to oppose a side surface of the recess; and
    when the replacement member is detachably mounted in the recess of the main body in the state of being separated from the cap in advance of when the nebulizer is to be used, and the cap is closed with respect to the main body, a protrusion portion that protrudes toward a main body side of the cap presses the bottom surface portion of the replacement member toward the bottom surface of the recess, and positions the replacement member in a vertical axis direction of the main body.

2. The mesh nebulizer according to claim 1, wherein
    the side surface of the recess of the main body increasingly opens toward a top; and
    the side wall portion of the replacement member increasingly opens toward the top so as to correspond to the side surface of the recess of the main body.

3. The mesh nebulizer according to claim 1, wherein the replacement member includes a finger grip portion that is continuous with an upper edge of the side wall portion and extends radially in a direction in a periphery of a center of the side wall portion.

4. The mesh nebulizer according to claim 3, wherein the finger grip portion extends in mutually opposite directions in the periphery of the center of the side wall portion.

5. The mesh nebulizer according to claim 3, wherein a groove that extends radially in a direction from the recess is provided in a periphery of an upper edge of the recess of the main body so as to correspond to the finger grip portion of the replacement member.

6. The mesh nebulizer according to claim 1, wherein
    the vibration surface is orthogonal to the vertical axis direction of the main body;
    the bottom surface of the recess of the main body is inclined with respect to the vertical axis direction of the main body; and
    the mesh portion and the bottom surface portion of the replacement member are inclined with respect to a center of the side wall portion so as to correspond to the bottom surface of the recess of the main body.

7. The mesh nebulizer according to claim 1, wherein a gasket is provided on the side surface of the recess of the main body so as to surround and be in contact with the side wall portion of the replacement member in a circumferential direction.

8. The mesh nebulizer according to claim 1, wherein the replacement member is made of synthetic resin.

9. The mesh nebulizer according to claim 1, wherein the cap is coupled to the main body via a hinge so as to be able to rotate.

10. A replacement member to be used to form a mesh nebulizer including a main body including a recess with a shape that is open upward, a vibration portion with a vibration surface arranged at a position corresponding to a bottom surface of the recess, and a liquid supply portion to supply liquid onto the vibration surface of the vibration portion, and a cap to openably and closeably cover an upper portion of the main body, the replacement member comprising:
    a film mesh portion that is to oppose the vibration surface;
    a bottom surface portion to support a circumferential edge of the mesh portion; and
    a side wall portion that is continuous with an outer edge of the bottom surface portion and is to oppose a side surface of the recess; wherein
    the replacement member is separate from the main body and the cap, and is to be detachably mounted in the recess of the main body in a state of being separated from the cap in advance of when the nebulizer is to be used; and
    when the replacement member is detachably mounted in the recess of the main body in the state of being separated from the cap in advance of when the nebulizer is to be used, and the cap is closed with respect to the main body, a protrusion portion that protrudes toward a main body side of the cap presses the bottom surface portion of the replacement member toward the bottom surface of the recess, and positions the replacement member in a vertical axis direction of the main body.

11. The replacement member according to claim 10, further comprising a finger grip portion that is continuous with an upper edge of the side wall portion and extends radially in a specific direction in a periphery of a center of the side wall portion.

12. The replacement member according to claim 11, wherein the finger grip portion extends in mutually opposite directions in the periphery of the center of the side wall portion.

* * * * *